United States Patent
Trock et al.

(10) Patent No.: US 9,795,732 B2
(45) Date of Patent: *Oct. 24, 2017

(54) DETECTING UNINTENTIONAL MOTOR MOTION AND INFUSION DEVICE INCORPORATING SAME

(71) Applicant: MEDTRONIC MINIMED, INC., Northridge, CA (US)

(72) Inventors: Adam S. Trock, Burbank, CA (US); Hsiao-Yu S. Kow, Ladera Ranch, CA (US); Nichole R. Mattson, Playa Del Rey, CA (US); Steve Chow, Northridge, CA (US); Alexander S. Campbell, Tarzana, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/229,004

(22) Filed: Aug. 4, 2016

(65) Prior Publication Data

US 2016/0339171 A1    Nov. 24, 2016

Related U.S. Application Data

(62) Division of application No. 13/946,441, filed on Jul. 19, 2013, now Pat. No. 9,433,731.

(51) Int. Cl.
*A61M 5/142* (2006.01)
*A61M 5/168* (2006.01)

(52) U.S. Cl.
CPC .... *A61M 5/14244* (2013.01); *A61M 5/14236* (2013.01); *A61M 5/16831* (2013.01);
(Continued)

(58) Field of Classification Search
CPC ............ A61M 5/16831; A61M 5/1685; A61M 2005/16863; A61M 2005/3306;
(Continued)

(56) References Cited

U.S. PATENT DOCUMENTS

| 3,631,847 A | 1/1972 | Hobbs, II |
| 4,212,738 A | 7/1980 | Henne |

(Continued)

FOREIGN PATENT DOCUMENTS

| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.

(Continued)

*Primary Examiner* — Bhisma Mehta
*Assistant Examiner* — William Frehe
(74) *Attorney, Agent, or Firm* — Lorenz & Kopf, LLP

(57) ABSTRACT

Apparatus are provided for infusion devices and related systems and operating methods. An exemplary system includes a motor, a sensing arrangement coupled to the motor to provide output indicative of a detected characteristic of the motor when the sensing arrangement is enabled, and a module coupled to the sensing arrangement to periodically enable the sensing arrangement while the motor is idle and detect potential unintended motion of the motor based on the output from the sensing arrangement while periodically enabling the sensing arrangement. In some embodiments, the motor includes a rotor configured such that its rotation provides translational displacement of a plunger in a fluid reservoir, and the sensing arrangement (Continued)

includes one or more sensors configured to provide output indicative of a detected magnetic field of the rotor magnet.

19 Claims, 7 Drawing Sheets

(52) U.S. Cl.
CPC ............... *A61M 2205/3317* (2013.01); *A61M 2205/3365* (2013.01); *A61M 2205/50* (2013.01); *A61M 2205/502* (2013.01); *A61M 2205/581* (2013.01); *A61M 2205/582* (2013.01); *A61M 2205/583* (2013.01); *A61M 2205/8212* (2013.01); *F04B 2201/0201* (2013.01); *F04B 2201/02011* (2013.01)

(58) Field of Classification Search
CPC ... A61M 2005/3317; A61M 2005/3365; F04B 2201/0201; F04D 15/0095
USPC .......................................................... 91/171
See application file for complete search history.

(56) References Cited

U.S. PATENT DOCUMENTS

| | | | |
|---|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 4,898,579 A | 2/1990 | Groshong |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,534,691 A * | 7/1996 | Holdaway .......... A61M 5/14228 250/231.14 |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,620,312 A * | 4/1997 | Hyman ................. A61M 5/142 417/474 |
| 5,626,144 A | 5/1997 | Tacklind et al. |
| 5,628,619 A | 5/1997 | Wilson |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |

(56) References Cited

U.S. PATENT DOCUMENTS

| | | |
|---|---|---|
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,248,093 B1 | 6/2001 | Moberg |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 8,474,332 B2 | 7/2013 | Bente, IV et al. |
| 9,433,731 B2 * | 9/2016 | Trock ................ A61M 5/16831 |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

(56) References Cited

OTHER PUBLICATIONS

Farkas-Hirsch R et al. (1994). Continuous Subcutaneous Insulin Infusion: A Review of the Past and its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed• Technologies.
(Intensive Diabetes Management, 1995). Insulin Infusion Pump Therapy. pp. 66-78.
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.

Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.

(56) References Cited

OTHER PUBLICATIONS

Nishida, Kenro, et al., "Clinical applications of teh wearable artificial endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

DETECTING UNINTENTIONAL MOTOR MOTION AND INFUSION DEVICE INCORPORATING SAME

CROSS-REFERENCE TO RELATED APPLICATIONS

This application is a division of U.S. patent application Ser. No. 13/946,441, filed Jul. 19, 2013.

TECHNICAL FIELD

Embodiments of the subject matter described herein relate generally to medical devices, and more particularly, embodiments of the subject matter relate to detecting unintentional motion of a motor in a portable electronic device, such as a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user.

In practice, it is desirable to conserve power consumption by portable or battery-powered electronic devices, such as portable fluid infusion devices, to prolong battery life. Brushless direct current (BLDC) electric motors may be appealing for some applications because of their relatively high efficiency and relatively compact size. However, the BLDC is potentially susceptible to magnetic interference by virtue of the permanent magnets on its rotor. For example, a relatively large magnetic field could potentially displace the rotor in an uncontrolled manner independently of the motor controller. Accordingly, it is desirable to protect against such uncontrolled displacement of the rotor without compromising efficiency.

BRIEF SUMMARY

An embodiment of a control system suitable for use with an infusion device is provided. An exemplary system includes a motor, a sensing arrangement coupled to the motor to provide output indicative of a detected characteristic of the motor when the sensing arrangement is enabled, and a module coupled to the sensing arrangement to periodically enable the sensing arrangement while the motor is idle and detect potential unintended motion of the motor based on the output from the sensing arrangement while periodically enabling the sensing arrangement.

In one embodiment, a method is provided for detecting potential unintended motion of a motor using a sensing arrangement. The sensing arrangement provides output indicative of a detected characteristic of the motor when the sensing arrangement is enabled. The method involves periodically enabling a sensing arrangement while the motor is idle and detecting the potential unintended motion based on outputs obtained from the sensing arrangement when periodically enabling the sensing arrangement while the motor is idle.

In another embodiment, an apparatus for an infusion device is provided. The infusion device includes a motor, a sensing arrangement, and a module. The motor includes a rotor having a magnet coupled thereto, wherein rotation of the rotor is configured to provide translational displacement of a plunger in a fluid reservoir. The sensing arrangement is coupled to the motor and includes one or more sensors configured to provide output indicative of a detected magnetic field of the rotor magnet when the sensing arrangement is enabled. The module is coupled to the sensing arrangement to periodically enable the sensing arrangement while the motor is idle and detect potential unintended rotation of the rotor based on outputs obtained from the sensing arrangement while periodically enabling the sensing arrangement while the motor is idle.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
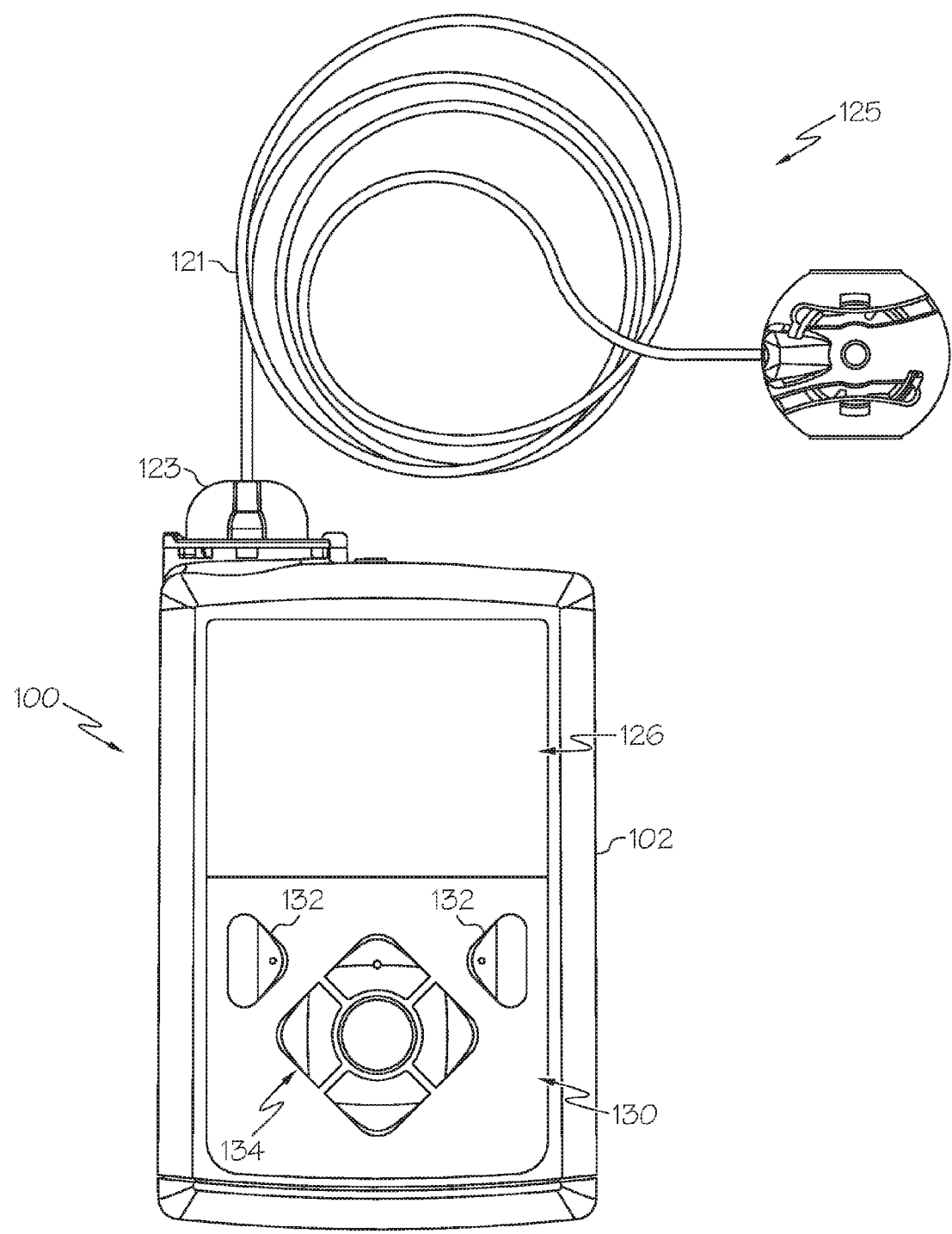
FIG. 1 depicts a plan view of an exemplary embodiment of a fluid infusion device suitable for use in an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Exemplary embodiments of the subject matter described herein generally relate to fluid infusion devices including a motor that is operable to linearly displace a plunger (or stopper) of a reservoir provided within the fluid infusion device, wherein the fluid infusion devices are configured to detect potential unintended motion of the motor when the motor is idle or otherwise not being operated. For example, to achieve improved efficiency, an idle motor may not consume current (or power) from an energy source when the motor is not being operated to deliver fluid from the reservoir. Thus, a rotor of the idle motor may be susceptible to unintended rotation by virtue of the absence of a stator magnetic field opposing rotation of the rotor. For example, an external magnetic field could potentially displace the rotor in an uncontrolled manner. Alternatively, an external magnetic field could potentially cause a change in the output of a sensing arrangement that detects the rotor magnetic field and provides a corresponding output indicative of the rotational position (or orientation) of the rotor. In such situations, an external magnetic field could cause the rotor sensing arrangement to indicate a rotation of the rotor without the rotor actually being rotated. Accordingly, the exemplary fluid infusion devices described herein are configured to periodically monitor the position (or orientation) of the motor while in the idle state to detect potential unintended motion, which could be either actual rotation of the rotor of the motor or a sensor output indicative of unintended rotation of the rotor.

As described in greater detail below, in one or more exemplary embodiments, the motor is realized as a brushless direct current (BLDC) motor having a permanent magnet fixedly coupled to its rotor, and as such, is susceptible to interference by external magnetic fields. A rotor sensing arrangement detects the rotor magnetic field and provides a corresponding output indicative of the rotational position (or orientation) of the rotor. While the motor is idle, the rotor sensing arrangement is periodically enabled or otherwise activated and the periodically obtained outputs from the rotor sensing arrangement are monitored to detect potential unintended rotation of the rotor. In exemplary embodiments, potential unintended rotation is detected or otherwise identified when a difference between a current (or most recently obtained) output from the rotor sensing arrangement and a reference output obtained from the rotor sensing arrangement upon enabling the rotor sensing arrangement for the periodic monitoring mode is not attributable to a boundary error. In this regard, when a boundary of the rotor magnetic field is aligned with a sensor of the rotor sensing arrangement, the sensor output may produce different (or varying) output states independently of rotation of the rotor. For example, the output of a Hall effect sensor may exhibit a nondeterministic rise/fall time when transitioning to/from a particular output state when the Hall effect sensor is aligned with a neutral boundary of the rotor magnetic field and produce different output states during periodic sampling in the absence of any non-negligible rotation of the rotor. Accordingly, during the periodic monitoring mode, boundary conditions (or sensor outputs indicative thereof) are effectively filtered by identifying a boundary error reference output from the rotor sensing arrangement that could be attributable to magnetic field boundary alignment error and detecting potential unintended rotation when the current (or most recently obtained) output from the rotor sensing arrangement is not equal to either the previously obtained reference output or the previously identified boundary error reference output. Thus, the difference between the current (or most recently obtained) output from the rotor sensing arrangement and the reference output is not attributable to the potential magnetic field boundary alignment error.

It should be noted that although the subject matter may be described herein in the context of BLDC motors and rotor sensing arrangements that detect the rotor magnetic field, the subject matter described herein is not necessarily limited to BLDC motors and/or rotor sensing arrangements that detect the rotor magnetic field. Accordingly, the subject matter described herein may be implemented in an equivalent manner using any suitable combination of motor and sensing arrangement capable of detecting a characteristic of the motor that is influenced by the motion, position, or orientation of the motor.

As described in greater detail below, when a potential unintended motion that is not attributable a boundary error is detected, a continuous monitoring mode is entered for a finite duration to determine whether the potential unintended motion exceeds any thresholds for particular monitoring criteria. In the continuous monitoring mode, the rotor sensing arrangement is continuously enabled and its output monitored throughout the finite duration of the continuous mode. Numerous different monitoring criteria may be implemented and utilized to track the unintended motion during the continuous monitoring mode to determine whether the extent of the unintended motion is actionable. In this regard, unintended motion that does not exceed thresholds for any monitoring criteria may be deemed as relatively minor unintended motion that is compensated for (e.g., by modifying subsequent operation of the motor in a manner that accounts for the unintended motion) without generating higher level alerts or notifications. Conversely, unintended motion that exceeds a threshold for a monitoring criterion is identified as actionable unintended motion. When actionable unintended motion is identified during the continuous mode, one or more higher level remedial actions are initiated to notify the user of the fluid infusion device of potentially abnormal operation of the fluid infusion device or otherwise operate the fluid infusion device in a manner that mitigates or otherwise prevents inadvertent overdelivery and/or underdelivery of fluid to the user.

Figure 2:
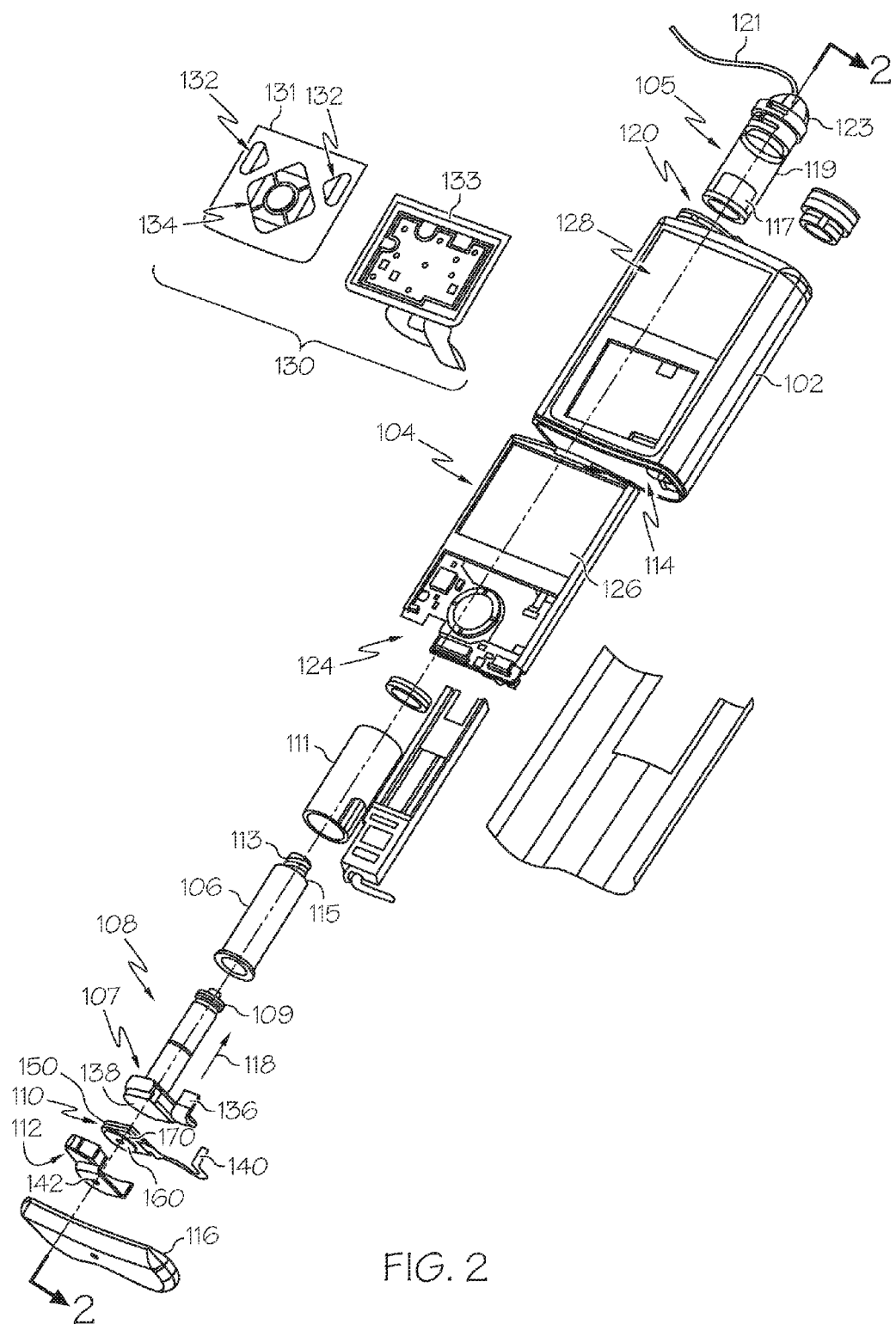
FIG. 2 is an exploded perspective view of the fluid infusion device of FIG. 1.
Figure 3:
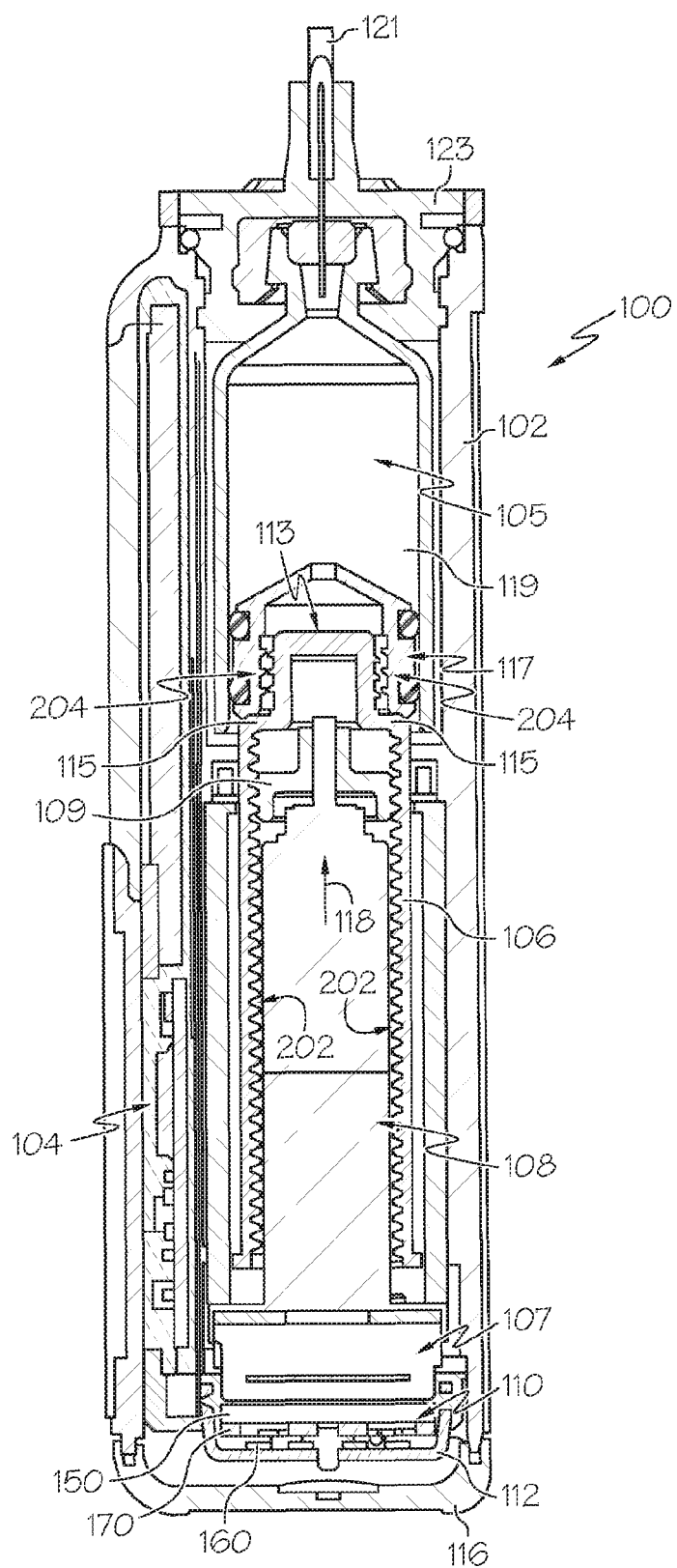
FIG. 3 is a cross-sectional view of the fluid infusion device of FIGS. 1-2 as viewed along line 2-2 in FIG. 2 when assembled with a reservoir inserted in the infusion device.

FIGS. 1-3 depict one exemplary embodiment of a fluid infusion device 100 (or alternatively, infusion pump) suitable for use in an infusion system. The fluid infusion device 100 is a portable medical device designed to be carried or worn by a patient (or user), and the fluid infusion device 100 may leverage a number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 1-3 depict some aspects of the infusion device 100 in a simplified manner; in practice, the infusion device 100 could include additional elements, features, or components that are not shown or described in detail herein.

As best illustrated in FIGS. 1-2, the illustrated embodiment of the fluid infusion device 100 includes a housing 102 adapted to receive a fluid-containing reservoir 105. An opening 120 in the housing 102 accommodates a fitting 123 (or cap) for the reservoir 105, with the fitting 123 being configured to mate or otherwise interface with tubing 121 of an infusion set 125 that provides a fluid path to/from the body of the user. In this manner, fluid communication from the interior of the reservoir 105 to the user is established via the tubing 121 in a conventional manner. The illustrated fluid infusion device 100 includes a human-machine interface (HMI) 130 (or user interface) that includes elements 132, 134 that can be manipulated by the user to administer a bolus of fluid (e.g., insulin), to change therapy settings, to change user preferences, to select display features, and the like. The infusion device also includes a display element 126, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 102 is formed from a substantially rigid material having a hollow interior 114 adapted to allow an electronics assembly 104, a sliding member (or slide) 106, a drive system 108, a sensor assembly 110, and a drive system capping member 112 to be disposed therein in addition to the reservoir 105, with the contents of the housing 102 being enclosed by a housing capping member 116. The opening 120, the slide 106, and the drive system 108 are coaxially aligned in an axial direction (indicated by arrow 118), whereby the drive system 108 facilitates linear displacement of the slide 106 in the axial direction 118 to dispense fluid from the reservoir 105 (after the reservoir 105 has been inserted into opening 120), with the sensor assembly 110 being configured to measure axial forces (e.g., forces aligned with the axial direction 118) exerted on the sensor assembly 110 responsive to operating the drive system 108 to displace the slide 106. In various embodiments, the sensor assembly 110 may be utilized to detect one or more of the following: an occlusion in a fluid path that slows, prevents, or otherwise degrades fluid delivery from the reservoir 105 to a user's body; when the reservoir 105 is empty; when the slide 106 is properly seated with the reservoir 105; when a fluid dose has been delivered; when the infusion pump 100 is subjected to shock or vibration; when the infusion pump 100 requires maintenance.

Depending on the embodiment, the fluid-containing reservoir 105 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 2-3, the reservoir 105 typically includes a reservoir barrel 119 that contains the fluid and is concentrically and/or coaxially aligned with the slide 106 (e.g., in the axial direction 118) when the reservoir 105 is inserted into the infusion pump 100. The end of the reservoir 105 proximate the opening 120 may include or otherwise mate with the fitting 123, which secures the reservoir 105 in the housing 102 and prevents displacement of the reservoir 105 in the axial direction 118 with respect to the housing 102 after the reservoir 105 is inserted into the housing 102. As described above, the fitting 123 extends from (or through) the opening 120 of the housing 102 and mates with tubing 121 to establish fluid communication from the interior of the reservoir 105 (e.g., reservoir barrel 119) to the user via the tubing 121 and infusion set 125. The opposing end of the reservoir 105 proximate the slide 106 includes a plunger 117 (or stopper) positioned to push fluid from inside the barrel 119 of the reservoir 105 along a fluid path through tubing 121 to a user. The slide 106 is configured to mechanically couple or otherwise engage with the plunger 117, thereby becoming seated with the plunger 117 and/or reservoir 105. Fluid is forced from the reservoir 105 via tubing 121 as the drive system 108 is operated to displace the slide 106 in the axial direction 118 toward the opening 120 in the housing 102.

In the illustrated embodiment of FIGS. 2-3, the drive system 108 includes a motor assembly 107 and a drive screw 109. The motor assembly 107 includes a motor that is coupled to drive train components of the drive system 108 that are configured to convert rotational motor motion to a translational displacement of the slide 106 in the axial direction 118, and thereby engaging and displacing the stopper 117 of the reservoir 105 in the axial direction 118. In some embodiments, the motor assembly 107 may also be powered to translate the slide 106 in the opposing direction (e.g., the direction opposite direction 118) to retract and/or detach from the reservoir 105 to allow the reservoir 105 to be replaced. In exemplary embodiments, the motor assembly 107 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 105.

As best shown in FIG. 3, the drive screw 109 mates with threads 202 internal to the slide 106. When the motor assembly 107 is powered and operated, the drive screw 109 rotates, and the slide 106 is forced to translate in the axial direction 118. In an exemplary embodiment, the infusion pump 100 includes a sleeve 111 to prevent the slide 106 from rotating when the drive screw 109 of the drive system 108 rotates. Thus, rotation of the drive screw 109 causes the slide 106 to extend or retract relative to the drive motor assembly 107. When the fluid infusion device is assembled and operational, the slide 106 contacts the plunger 117 to engage the reservoir 105 and control delivery of fluid from the infusion pump 100. In an exemplary embodiment, the shoulder portion 115 of the slide 106 contacts or otherwise engages the plunger 117 to displace the plunger 117 in the axial direction 118. In alternative embodiments, the slide 106 may include a threaded tip 113 capable of being detachably engaged with internal threads 204 on the plunger 117 of the reservoir 105, as described in detail in U.S. Pat. Nos. 6,248,093 and 6,485,465, which are incorporated by reference herein.

As illustrated in FIG. 2, the electronics assembly 104 includes control electronics 124 coupled to the display element 126, with the housing 102 including a transparent window portion 128 that is aligned with the display element 126 to allow the display 126 to be viewed by the user when the electronics assembly 104 is disposed within the interior 114 of the housing 102. The control electronics 124 generally represent the hardware, firmware, processing logic and/or software (or combinations thereof) configured to control operation of the motor assembly 107 and/or drive system 108, as described in greater detail below in the context of FIG. 4. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 124 includes one or more programmable controllers that may be programmed to control operation of the infusion pump 100.

The motor assembly 107 includes one or more electrical leads 136 adapted to be electrically coupled to the electronics assembly 104 to establish communication between the control electronics 124 and the motor assembly 107. In response to command signals from the control electronics 124 that operate a motor driver (e.g., a power converter) to regulate the amount of power supplied to the motor from a power supply, the motor actuates the drive train components of the drive system 108 to displace the slide 106 in the axial direction 118 to force fluid from the reservoir 105 along a fluid path (including tubing 121 and an infusion set), thereby administering doses of the fluid contained in the reservoir 105 into the user's body. Preferably, the power supply is realized one or more batteries contained within the housing 102. Alternatively, the power supply may be a solar panel, capacitor, AC or DC power supplied through a power cord, or the like. In some embodiments, the control electronics 124 may operate the motor of the motor assembly 107 and/or drive system 108 in a stepwise manner, typically on an intermittent basis; to administer discrete precise doses of the fluid to the user according to programmed delivery profiles.

Referring to FIGS. 1-2, as described above, the user interface 130 includes HMI elements, such as buttons 132 and a directional pad 134, that are formed on a graphic keypad overlay 131 that overlies a keypad assembly 133, which includes features corresponding to the buttons 132, directional pad 134 or other user interface items indicated by the graphic keypad overlay 131. When assembled, the keypad assembly 133 is coupled to the control electronics 124, thereby allowing the HMI elements 132, 134 to be manipulated by the user to interact with the control electronics 124 and control operation of the infusion pump 100, for example, to administer a bolus of insulin, to change therapy settings, to change user preferences, to select display features, to set or disable alarms and reminders, and the like. In this regard, the control electronics 124 maintains and/or provides information to the display 126 regarding program parameters, delivery profiles, pump operation, alarms, warnings, statuses, or the like, which may be adjusted using the HMI elements 132, 134. In various embodiments, the HMI elements 132, 134 may be realized as physical objects (e.g., buttons, knobs, joysticks, and the like) or virtual objects (e.g., using touch-sensing and/or proximity-sensing technologies). For example, in some embodiments, the display 126 may be realized as a touch screen or touch-sensitive display, and in such embodiments, the features and/or functionality of the HMI elements 132, 134 may be integrated into the display 126 and the HMI 130 may not be present. In some embodiments, the electronics assembly 104 may also include alert generating elements coupled to the control electronics 124 and suitably configured to generate one or more types of feedback, such as, without limitation: audible feedback; visual feedback; haptic (physical) feedback; or the like.

Referring to FIGS. 2-3, in accordance with one or more embodiments, the sensor assembly 110 includes a back plate structure 150 and a loading element 160. The loading element 160 is disposed between the sensor capping member 112 and a beam structure 170 that includes one or more beams having sensing elements disposed thereon that are influenced by compressive force applied to the sensor assembly 110 that deflects the one or more beams, as described in greater detail in U.S. patent application Ser. No. 12/908,807, which is incorporated by reference herein. In exemplary embodiments, the back plate structure 150 is affixed, adhered, mounted, or otherwise mechanically coupled to the bottom surface 138 of the drive system 108 such that the back plate structure 150 resides between the bottom surface 138 of the drive system 108 and the housing cap 116. The drive system capping member 112 is contoured to accommodate and conform to the bottom of the sensor assembly 110 and the drive system 108. The drive system capping member 112 may be affixed to the interior of the housing 102 to prevent displacement of the sensor assembly 110 in the direction opposite the direction of force provided by the drive system 108 (e.g., the direction opposite direction 118). Thus, the sensor assembly 110 is positioned between the motor assembly 107 and secured by the capping member 112, which prevents displacement of the sensor assembly 110 in a downward direction opposite the direction of arrow 118, such that the sensor assembly 110 is subjected to a reactionary compressive force when the drive system 108 and/or motor assembly 107 is operated to displace the slide 106 in the axial direction 118 in opposition to the fluid pressure in the reservoir 105. Under normal operating conditions, the compressive force applied to the sensor assembly 110 is correlated with the fluid pressure in the reservoir 105. As shown, electrical leads 140 are adapted to electrically couple the sensing elements of the sensor assembly 110 to the electronics assembly 104 to establish communication to the control electronics 124, wherein the control electronics 124 are configured to measure, receive, or otherwise obtain electrical signals from the sensing elements of the sensor assembly 110 that are indicative of the force applied by the drive system 108 in the axial direction 118.

Figure 4:
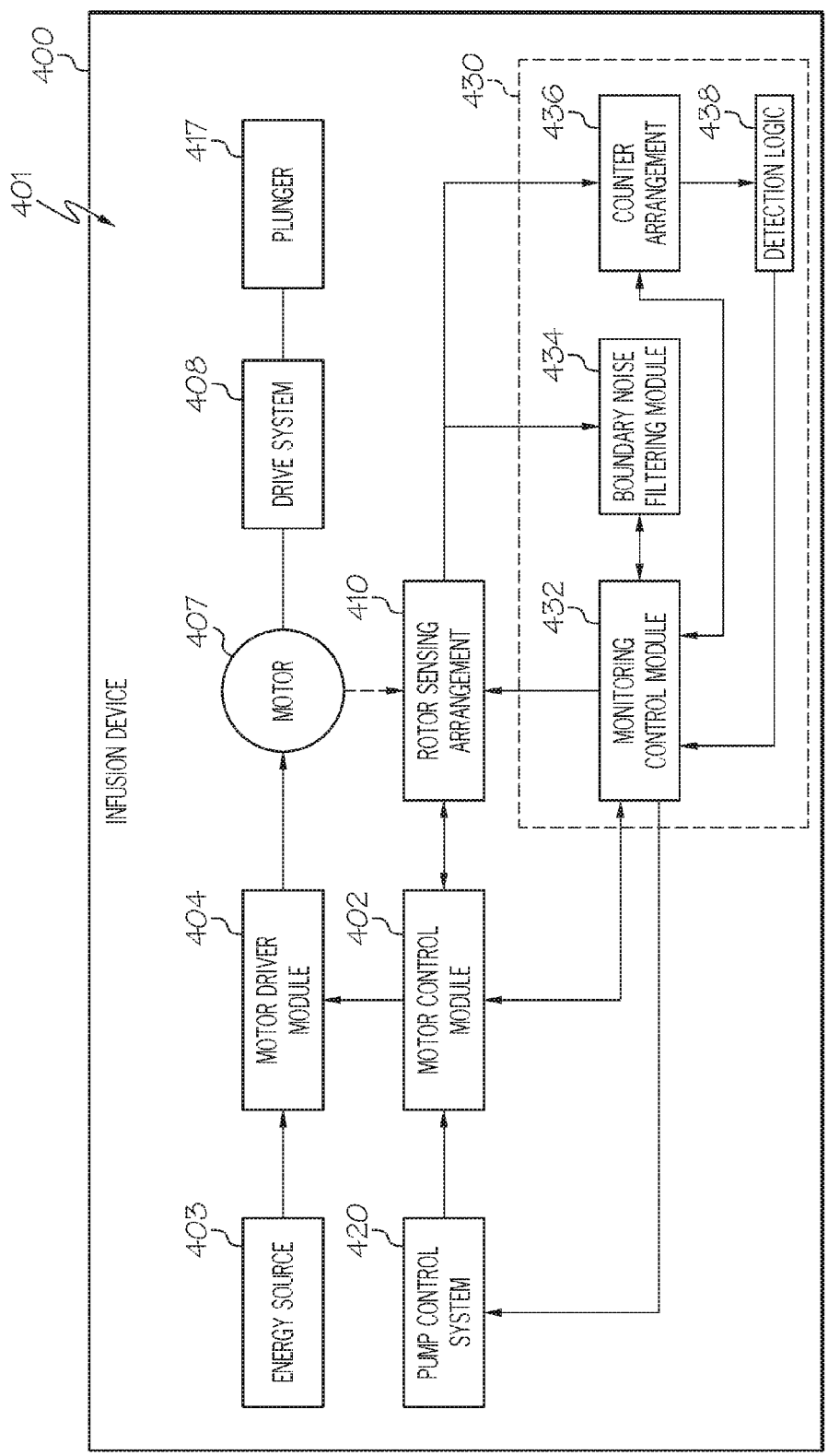
FIG. 4 is a block diagram of an exemplary control system suitable for use in a fluid infusion device, such as the fluid infusion device of FIG. 1.

FIG. 4 depicts an exemplary embodiment of a control system 401 suitable for use with an infusion device 400, such as infusion device 100. The control system 401 includes a motor control module 402 coupled to a motor driver module 404 that is coupled between an energy source 403 and a motor 407 (e.g., motor assembly 107). The motor control module 402 generates or otherwise provides command signals that operate the motor driver module 404 to provide current (or power) from the energy source 403 to the motor 407 to displace a plunger 417 (e.g., plunger 117) of a reservoir (e.g., reservoir 105) and provide a desired amount of fluid to a user in response to receiving, from a pump control system 420, a dosage command indicative of the desired amount of fluid to be delivered. In this regard, the pump control system 420 generally represents the electronics and other components that control operation of the fluid infusion device 400 according to a desired infusion delivery program in a manner that is influenced by sensor data pertaining to a condition of a user (e.g., the user's current glucose level) and/or in a manner that is dictated by the user. In exemplary embodiments, the control system 401 also includes a monitoring module 430 that is coupled to a rotor sensing arrangement 410 to detect or otherwise identify unintentional rotation of the rotor of the motor 407 based on outputs from the rotor sensing arrangement 410, as described in greater detail below.

It should be understood that FIG. 4 is a simplified representation of the control system 401 for purposes of explanation and is not intended to limit the subject matter described herein in any way. For example, in practice, the features and/or functionality of the motor control module 402 may implemented by or otherwise integrated into the pump control system 420, or vice versa. Similarly, the features and/or functionality of the monitoring module 430 may implemented by or otherwise integrated into the motor control module 402. In some embodiments, the features and/or functionality of the pump control system 420 may be implemented by control electronics 124 located in the fluid infusion device 100, 400, while in alternative embodiments, the pump control system 420 may be implemented by a remote computing device that is physically distinct and/or separate from the infusion device 400.

In exemplary embodiments, the energy source 403 is realized as a battery housed within the infusion device 400 (e.g., within housing 102) that provides direct current (DC) power. In this regard, the motor driver module 404 generally represents the combination of circuitry, hardware and/or other electrical components configured to convert or otherwise transfer DC power provided by the energy source 403 into alternating electrical signals applied to respective phases of the stator windings of the motor 407 that result in current flowing through the stator windings that generates a stator magnetic field and causes the rotor of the motor 407 to rotate. In this regard, the motor control module 402 generally represents the hardware, circuitry, logic, firmware and/or other combination of components of the control electronics 124 that is configured to receive or otherwise obtain a commanded dosage from the pump control system 420, convert the commanded dosage to a commanded translational displacement of the plunger 417, and command, signal, or otherwise operate the motor driver module 404 to cause the rotor of the motor 407 to rotate by an amount that produces the commanded translational displacement of the plunger 417. For example, the motor control module 402 may determine an amount of rotation of the rotor required to produce translational displacement of the plunger 417 that achieves the commanded dosage received from the pump control system 420, and based on the current rotational position (or orientation) of the rotor with respect to the stator indicated by the output of the rotor sensing arrangement 410, the motor control module 402 determines the appropriate sequence of alternating electrical signals to be applied to the respective phases of the stator windings to rotate the rotor by that determined amount of rotation from its current position (or orientation). In this regard, when the motor 407 is a BLDC motor, the alternating electrical signals are determined to commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 402 operates the motor driver module 404 to apply the determined alternating electrical signals (e.g., the command signals) to the stator windings of the motor 407 to achieve the desired delivery of fluid to the user.

When the motor control module 402 is operating the motor driver module 404, current flows from the energy source 403 through the stator windings of the motor 407 to produce a stator magnetic field that interacts with the rotor magnetic field. As described in greater detail below, in exemplary embodiments, after the motor control module 402 operates the motor driver module 404 and/or motor 407 to achieve the commanded dosage, the motor control module 402 ceases operating the motor driver module 404 and/or motor 407 until a subsequent dosage command is received. In this regard, the motor driver module 404 and the motor 407 enter an idle state during which the motor driver module 404 effectively disconnects or isolates the stator windings of the motor 407 from the energy source 403. In other words, current does not flow from the energy source 403 through the stator windings of the motor 407 when the motor 407 is idle, and thus, the motor 407 does not consume power from the energy source 403 in the idle state, thereby improving efficiency.

Depending on the embodiment, the motor control module 402 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 402, or in any practical combination thereof. In exemplary embodiments, the motor control module 402 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 402. The computer-executable programming instructions, when read and executed by the motor control module 402, cause the motor control module 402 to perform the tasks, operations, functions, and processes described in greater detail below.

Figure 5:
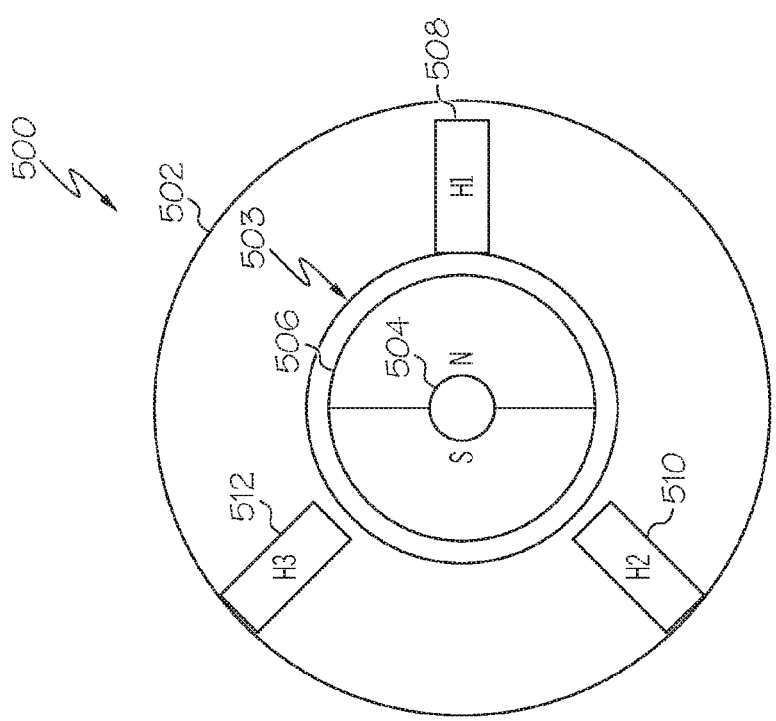
FIG. 5 is a top view of an exemplary motor and corresponding rotor sensing arrangement suitable for use in the control system of FIG. 4.

FIG. 5 depicts a top view of an exemplary motor 500 suitable for use as a motor 107, 407 in an infusion device 100, 400. The illustrated motor 500 includes a cylindrical stator 502 with a hollow interior 503 having a cylindrical rotor 504 (or rotary shaft) disposed therein. It should be appreciated that the subject matter described herein is not limited to an inner rotor construction, and in alternative embodiments, the motor 500 may be realized with an outer rotor construction. The rotor 504 engages or is otherwise mechanically coupled to a drive system 108, 408 that translates the rotation of the rotor 504 with respect to the stator 502 into translational displacement of the slide 106 and/or plunger 117, 417, as described above. In exemplary embodiments, the motor 500 is a BLDC motor having one or more permanent magnets 506 mounted, affixed, or otherwise fixedly coupled to the rotor 504 so that the permanent magnet 506 and the rotor 504 rotate in unison. The illustrated motor 500 is a 3-phase BLDC motor having 3-phase stator windings (not illustrated) that are wound about the stator 502 (e.g., via teeth and/or slots in the stator core) in a conventional manner.

Referring now to FIGS. 4-5, in exemplary embodiments, the rotor sensing arrangement 410 includes a plurality of Hall effect sensors 508, 510, 512 that are positioned about the rotor magnet 506 (e.g., by mounting the Hall sensors 508, 510, 512 to the stator 502) to detect the magnetic field of the rotor magnet 506, and thereby, the rotational position (or orientation) of the rotor 504 with respect to the stator 502 based on the detected rotor magnetic field orientation. For a 3-phase BLDC motor 407, 500, three Hall sensors 508, 510, 512 are disposed circumferentially about the rotor 504 at substantially even intervals (e.g., 120° or $2\pi/3$ radians), as illustrated in FIG. 5, thereby allowing the state of a respective Hall sensor 508, 510, 512 to correspond to a respective phase of the stator windings. For the illustrated embodiment, the output of the first Hall sensor 508 corresponds to a first logic state (e.g., a logical high voltage or logic '1') by virtue of it being aligned with the magnetic north of the rotor magnet 506 while the outputs of the second and third Hall sensors 510, 512 correspond to the opposite logic state (e.g., a logical low voltage or logic '0') by virtue of being aligned with the magnetic south of the rotor magnet 506. As described above, the motor control module 402 is coupled to the Hall sensors 508, 510, 512 to obtain their outputs, determine the rotational position of the rotor 504 with respect to the stator 502 based on the logic states of the Hall sensors 508, 510, 512, and thereby determine the commutation sequence for the stator winding phases that achieves a desired amount and direction of rotation of the rotor 504 from its current rotational position to deliver the command dosage of fluid to the user.

Still referring to FIGS. 4-5, in exemplary embodiments, the rotor sensing arrangement 410 and/or Hall sensors 508, 510, 512 are coupled to the energy source 403 such that the sensing elements of the rotor sensing arrangement 410 and/or Hall sensors 508, 510, 512 consume power (or current) from the energy source 403 when the rotor sensing arrangement 410 and/or Hall sensors 508, 510, 512 are powered on, activated, or otherwise enabled. In this regard, in exemplary embodiments, the Hall sensors 508, 510, 512 are capable of being disabled by the motor control module 402 to conserve power when the motor 407 is in the idle state and the motor control module 402 does not require the outputs of the rotor sensing arrangement 410 to operate the motor 407, 500. For example, the Hall sensors 508, 510, 512 may be realized as an integrated circuit (or chip) having an enable input pin, pad, terminal, or the like that is associated with an internal switching arrangement that is capable of selectively allowing/preventing current flow from the energy source 403 to the sensing elements of the Hall sensors 508, 510, 512.

In this regard, prior to operating the motor driver module 404 and/or motor 407, 500, the motor control module 402 may apply a logical high voltage signal (or logic '1') to the enable input pins of the Hall sensors 508, 510, 512 to turn on or otherwise activate the switching arrangements, which, in turn, allow current flow from the energy source 403 to the sensing elements of the rotor sensing arrangement 410 and/or Hall sensors 508, 510, 512, thereby powering on, activating, or otherwise enabling the rotor sensing arrangement 410. Thereafter, the motor control module 402 determines the position (or orientation) of the rotor 504 and determines how to operate the motor driver module 404 and rotate the rotor 504 of the motor 407, 500 to achieve a commanded dosage based on the position (or orientation) of the rotor 504 indicated by the rotor sensing arrangement 410 and/or Hall sensors 508, 510, 512. After operating the motor driver module 404 and/or motor 407, 500, the motor control module 402 applies a logical low voltage signal (or logic '0') to the enable input pins of the Hall sensors 508, 510, 512 to power off, deactivate, or otherwise disable rotor sensing arrangement 410 and/or Hall sensors 508, 510, 512 and prevent current flow from the energy source 403 to the sensing elements of the rotor sensing arrangement 410 and/or Hall sensors 508, 510, 512. Accordingly, when the motor control module 402 is not operating the motor driver module 404 and the motor 407, 500 is in an idle state, power (or current) from the energy source 403 is not consumed by the stator windings of the motor 407, 500 or the rotor sensing arrangement 410 and/or Hall sensors 508, 510, 512.

By virtue of the magnet 506 being fixedly coupled to and rotating in unison with the rotor 504, the presence of an external magnetic field proximate the infusion device 400 when current is not applied to the stator windings may cause the magnet 506 to rotate absent an opposing stator magnetic field, which, in turn, could potentially rotate the rotor 504 and thereby displace the plunger 417 via drive system 408. Accordingly, the monitoring module 430 is coupled to the rotor sensing arrangement 410 and/or Hall sensors 508, 510, 512 to detect or otherwise identify such unintended (or uncontrolled) rotation of the rotor 504 of the motor 407, 500 and take remedial action to prevent or otherwise mitigate unintended rotation. The illustrated monitoring module 430 includes, without limitation, a monitoring control module 432, a boundary noise filtering module 434, a counter arrangement 436, and detection logic 438.

It should be noted that although FIG. 4 depicts the elements of the illustrated monitoring module 430 as being distinct or separate from one another, in practice, the features and/or functionality of one or more elements of the monitoring module 430 may implemented by or otherwise integrated into a single element (e.g., the motor control module 402). Depending on the embodiment, the monitoring module 430 and/or the elements thereof may be implemented using any suitable hardware, circuitry, logic, firmware and/or combination thereof configured to support the tasks, functions, operations and/or processes described herein. Furthermore, in some embodiments, the elements of the monitoring module 430 may be realized as software, and in such embodiments, the monitoring module 430 accesses a non-transitory computer-readable medium capable of storing programming instructions for execution that, when read and executed, cause the monitoring module 430 to generate the monitoring control module 432, the boundary noise filtering module 434, the counter arrangement 436, and/or detection logic 438.

In the illustrated embodiment, the monitoring control module 432 is coupled to the motor control module 402 and the rotor sensing arrangement 410 and/or Hall sensors 508, 510, 512 to implement a periodic monitoring (or periodic polling) mode by periodically enabling the rotor sensing arrangement 410 and/or Hall sensors 508, 510, 512 when the motor 407, 500 is idle (e.g., when the motor control module 402 is not operating the motor driver module 404). The boundary noise filtering module 434 is coupled to the monitoring control module 432 to filter or otherwise differentiate measured (or sensed) rotation of the rotor 504 that may be attributable to magnetic field boundary alignment error while the rotor sensing arrangement 410 and/or Hall sensors 508, 510, 512 are being operated in the periodic monitoring mode and detect or otherwise identify a potential unintended rotation that is not attributable to the boundary error. In response to receiving indication of a potential unintentional rotation from the boundary noise filtering module 434, the monitoring control module 432 continuously enables the rotor sensing arrangement 410 and/or Hall sensors 508, 510, 512 for a continuous monitoring mode having a finite duration and activates or otherwise enables the counter arrangements 436 to track uncontrolled rotation of the rotor 504 in accordance with various monitoring criteria while the motor 407, 500 is idle during the continuous monitoring mode. The detection logic 438 is coupled to the outputs of the counters of the counter arrangement 436 and detects or otherwise identifies an actionable unintended rotation of the rotor 504 during the continuous monitoring mode when one of the outputs of the counter arrangement 436 exceeds its associated threshold. The monitoring control module 432 is coupled to the detection logic 438, and in response to receiving indication of actionable unintended rotation that exceeds a threshold, provides a notification to the pump control system 420 so that an appropriate remedial action may be initiated.

Figure 6:
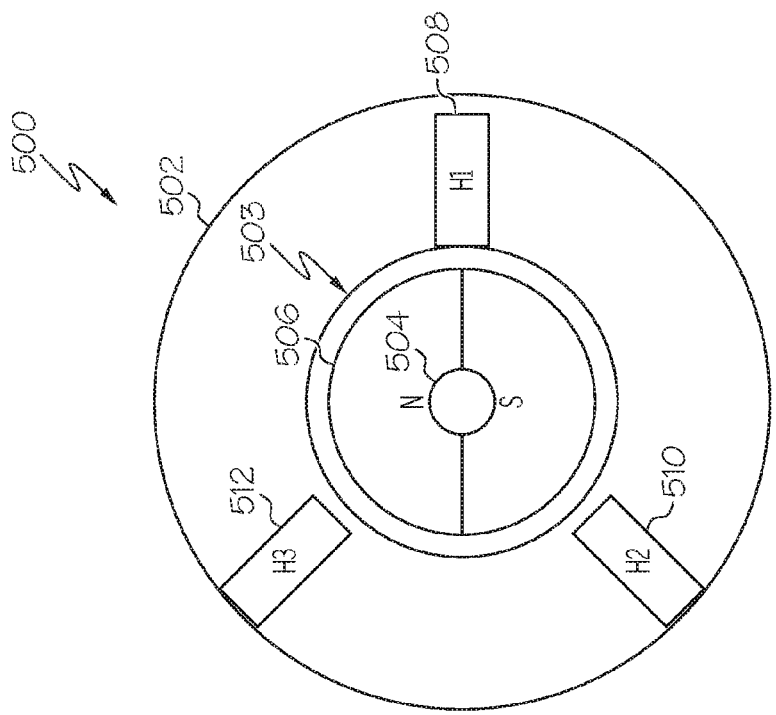
FIG. 6 is a top view of the motor and rotor sensing arrangement of FIG. 5 illustrating alignment of a rotor magnetic field boundary with a sensor of the rotor sensing arrangement in accordance with one embodiment.

In exemplary embodiments, the boundary noise filtering module 434 includes one or more data storage elements capable of storing reference outputs obtained from the rotor sensing arrangement 410 and/or Hall sensors 508, 510, 512 along with logic that compares the most recently obtained (or current) output from the rotor sensing arrangement 410 and/or Hall sensors 508, 510, 512 to the stored outputs to identify a difference between the most recently obtained sensor outputs and the stored sensor outputs that indicates a rotor rotation that is not attributable to boundary error. In this regard, in practice, one of the Hall sensors 508, 510, 512 may be aligned with a magnetic field boundary of the rotor magnet 506 such that a negligible rotation of the rotor 504 could cause the state of that sensor output to change in a nondeterministic manner that would otherwise indicate unintentional rotation of the rotor 504. For example, as illustrated in FIG. 6, after the motor control module 402 operates the motor 407, 500, the rotor 504 may stop rotating at an orientation with respect to the stator 502 that results in the magnetic field boundary of the rotor magnet 506 being aligned with the first Hall sensor 508. Thus, the first Hall sensor 508 could output a logical high state (e.g., a logical high voltage or logic '1') or a logical low state (e.g., a logical low voltage or logic '0') and/or alternate between logic states without the rotor 504 rotating by a non-negligible amount. For example, in the periodic mode, an initial sampling (or polling) of the outputs of the Hall sensors 508, 510, 512 may indicate the rotor 504 is at the '101' orientation (e.g., rotor magnetic north aligned with both Hall sensors 508, 512 while rotor magnetic south is aligned with Hall sensor 510), while a subsequent sampling may indicate the rotor 504 is at the '001' orientation (e.g., rotor magnetic south aligned with both Hall sensors 508, 510 while rotor magnetic north is aligned with Hall sensor 512) even though the actual rotation of the rotor 504 relative to its initial orientation is negligible.

Upon initiation of the periodic monitoring mode, the boundary noise filtering module 434 stores the initial sensor outputs sampled or otherwise obtained by the boundary noise filtering module 434 as a first reference sensor output state in a first data storage element, such as a register. For each periodic sampling of the sensor outputs, the boundary noise filtering module 434 compares the most recently obtained sensor outputs to the stored initial reference sensor outputs to determine whether a difference between the initial sensor output state and the current sensor output state indicates a potential rotation of the rotor 504 that is not attributable to magnetic field boundary alignment error. In this regard, when the sensor outputs at a subsequent sampling indicate a single incremental rotation in either direction from the initial rotor orientation (e.g., a change in the output state of only one Hall sensor 508, 510, 512 relative to the stored initial sensor output state), the boundary noise filtering module 434 stores that sensor output state as a boundary error reference sensor output state in a second data storage element. Thereafter, when sensor outputs at subsequent samplings are equal to either of the initial sensor output state or the boundary error reference output state, the boundary noise filtering module 434 does not identify unintentional rotation of the rotor 504. In this regard, one incremental rotation relative to the initial sensor output state is ignored and attributed to likely magnetic field boundary alignment error. Conversely, when sensor outputs at a subsequent sampling are not equal to either the initial sensor output state or the boundary error reference sensor output state, the boundary noise filtering module 434 detects or otherwise identifies a potential unintentional rotation of the rotor 504 that is not attributable to boundary alignment error and provides a notification to the monitoring control module 432.

For example, referring again to FIG. 6, the outputs of the Hall sensors 508, 510, 512 may indicate '101' orientation for the initial sampling in the periodic monitoring mode, wherein the boundary noise filtering module 434 stores '101' in a register corresponding to the initial sensor output state. Thereafter, when the outputs of the Hall sensors 508, 510, 512 indicate the '101' orientation for subsequent samplings in the periodic monitoring mode, the boundary noise filtering module 434 does not identify unintentional rotation of the rotor 504 and provides a logical low signal to the monitoring control module 432. If the sensor outputs at a subsequent sampling in the periodic monitoring mode indicate '001', the boundary noise filtering module 434 identifies the single incremental rotation from the '101' orientation and stores the '001' in the register corresponding to the boundary error reference state and continues providing a logical low signal to the monitoring control module 432. Thereafter, when sensor outputs at subsequent samplings are equal to the '101' orientation or the '001' orientation, the boundary noise filtering module 434 determines any rotation of the rotor 504 is likely attributable to the rotor magnetic field boundary being aligned with a Hall sensor 508 and continues providing a logical low signal to the monitoring control module 432. Conversely, once the sensor outputs at a subsequent sampling is not equal to the '101' orientation or the '001' orientation, the boundary noise filtering module 434 determines any rotation of the rotor 504 is not likely to be attributable to the rotor magnetic field boundary being aligned with a Hall sensor 508 and more likely attributable non-negligible unintentional rotation and provides a logical high signal to the monitoring control module 432. In this manner, the boundary noise filtering module 434 ensures that the rotor 504 rotates by at least one detectable incremental rotation (e.g., 60° in the embodiments of FIGS. 5-6) before providing a logical high signal to the monitoring control module 432.

Still referring to FIG. 4, in response to receiving notification of a potential unintended rotation from the boundary noise filtering module 434, the monitoring control module 432 activates or otherwise enables counters of the counter arrangement 436 that track changes in the sensor output states for the duration of a continuous monitoring mode. As described in greater detail below in the context of FIGS. 7-8, in exemplary embodiments, the counter arrangement 436 includes a first counter (the "rotation counter") configured to count the number of times the sensor output changes relative to a preceding sensor output state (e.g., the number of times the sensor output indicates a rotation in any direction since the preceding sample). A second counter (the "net displacement counter") of the counter arrangement 436 is configured to count the cumulative net difference in sensor output state (e.g., the difference between the most recently obtained sensor output state and a reference sensor output state). A third counter (the "sudden motion counter") of the counter arrangement 436 is configured to count the number of times a sudden unintended motion of the rotor 504 has occurred. For example, in one embodiment, the sudden motion counter counts the number of times the most recently sampled sensor output state indicates one half of a revolution relative to the preceding sampled sensor output state (e.g., the number of half revolutions between successive samplings).

In exemplary embodiments, the monitoring control module 432 is coupled to the motor control module 402 to receive indication of when the motor control module 402 begins operating the motor 407, 500 after an idle state, and in response, the monitoring control module 432 resets the rotation counter and the net displacement counter when the motor 407, 500 is operated by the motor control module 402. Additionally, in exemplary embodiments, the monitoring control module 432 periodically resets the sudden motion counter at a regular interval (e.g., hourly) independently of the motor control module 402 operating the motor 407, 500, however, it will be appreciated that the monitoring control module 432 may utilize some other criteria to dictate or otherwise determine when to reset the sudden motion counter in alternative embodiments.

The detection logic 438 is coupled to the outputs of the counters of the counter arrangement 436 and compares each output to a respective threshold to determine whether the respective condition being monitored has exceeded a threshold value or occurred more than a threshold number of times, and when a respective counter value exceeds its associated threshold, the detection logic 438 detects or otherwise identifies actionable unintentional rotation. In this regard, the thresholds are chosen to accommodate relatively minor unintended rotations of the rotor that can be compensated for by adjusting subsequent fluid delivery commands and are not indicative of relatively large and/or persistent magnetic interference. In this regard, the net rotational displacement threshold is chosen to detect rotational displacement in a particular direction that is likely to be caused by a relatively large external magnetic field, counted rotations threshold is chosen to detect persistent magnetic interference, and the sudden motion threshold is chosen to detect frequent relatively large sudden rotations. In accordance with one embodiment, the detection logic 438 is configured to detect or otherwise identify excessive unintentional rotation when either the net rotational displacement indicated by the net displacement counter is greater than two-thirds of a revolution, the rotor 504 rotations indicated by the rotation counter is greater than ten rotations, or the number of half revolutions indicated by the sudden motion counter is greater than three over a one hour period.

In exemplary embodiments, in response to the detection logic 438 detecting actionable unintended rotation, the monitoring control module 432 generates or otherwise provides a notification of the actionable unintended rotation to the pump control system 420. As described in greater detail below, the pump control system 420 may initiate one or more remedial actions (e.g., generating an alert for the user, adjusting subsequent dosage commands, rewinding the motor to retract the plunger, or the like) in response to receiving the actionable unintended rotation notification from the monitoring control module 432. Conversely, when the detection logic 438 fails to detect actionable unintended rotation during the duration of the continuous monitoring mode, the monitoring control module 432 may obtain the value of the net displacement counter and provide the value to the motor control module 402 to adjust subsequent deliveries in a manner that compensates for relatively minor unintentional the rotational displacement when converting the subsequent dosage command to commanded rotor rotations. For example, if net displacement counter indicates that the rotor 504 rotated by two incremental rotations in the direction opposite the delivery rotational direction, the motor control module 402 may add two incremental rotations to the determined number of incremental rotations corresponding to the received dosage command to prevent underdelivery. Likewise, if net displacement counter indicates that the rotor 504 rotated by two incremental rotations in the delivery rotational direction, the motor control module 402 may subtract two incremental rotations to the determined number of incremental rotations corresponding to the received dosage command to prevent overdelivery.

Still referring to FIG. 4, in accordance with one or more embodiments, the counter arrangement 436 also includes a counter configured to count a number of times the sensor outputs indicate an invalid state (e.g., all outputs of the Hall sensors 508, 510, 512 are the same logic state). In this regard, a relatively large external magnetic field could effectively cancel out one polarity of the rotor magnet 506 such that all Hall sensors 508, 510, 512 concurrently detect the same polarity. For example, referring again to FIG. 5, a large external south magnetic field could cause Hall sensor 508 to output a logical low signal concurrently to Hall sensors 510, 512. In this regard, the detection logic 438 compares the invalid state counter to a threshold number to detect when the invalid state persists for a particular duration (e.g., 2 seconds). In response to receiving notification of a persistent invalid state from the detection logic 438, the monitoring control module 432 generates or otherwise provides a notification of the persistent invalid state to the pump control system 420, which may initiate one or more remedial actions (e.g., notifying the user to confirm the infusion device 400 is not in the vicinity of a source of magnetic interference).

Figure 7:
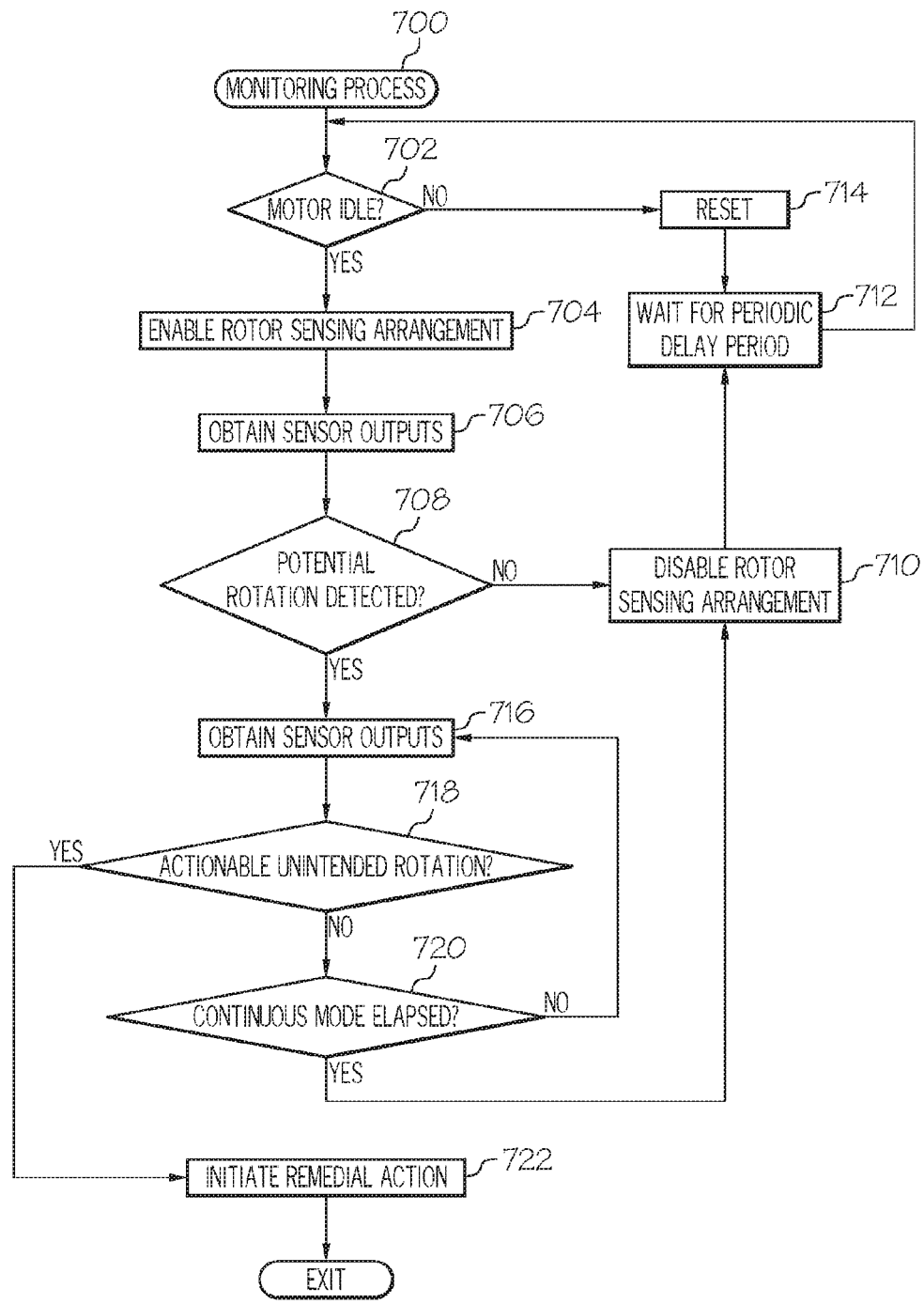
FIG. 7 is a flow diagram of an exemplary monitoring process suitable for use with the control system of FIG. 4.

FIG. 7 depicts an exemplary monitoring process 700 suitable for implementation by a control system in a fluid infusion device to detect unintentional motor motion. The various tasks performed in connection with the monitoring process 700 may be performed by hardware, firmware, software, or any combination thereof. For illustrative purposes, the following description refers to elements mentioned above in connection with FIGS. 1-6. In practice, portions of the monitoring process 700 may be performed by different elements of the control system 401, such as, for example, the motor control module 402, the motor driver module 404, the pump control system 420, the monitoring module 430, the monitoring control module 432, the boundary noise filtering module 434, the counter arrangement 436, the detection logic 438, the rotor sensing arrangement 410 and/or the Hall sensors 508, 510, 512. It should be appreciated that the monitoring process 700 may include any number of additional or alternative tasks, the tasks need not be performed in the illustrated order and/or the tasks may be performed concurrently, and/or the monitoring process 700 may be incorporated into a more comprehensive procedure or process having additional functionality not described in detail herein. Moreover, one or more of the tasks shown and described in the context of FIG. 7 could be omitted from a practical embodiment of the monitoring process 700 as long as the intended overall functionality remains intact.

In exemplary embodiments, the monitoring process 700 initializes or otherwise begins in a periodic monitoring mode, wherein the outputs of the rotor position sensors are periodically sampled or polled while the motor is in the idle state or otherwise not being operated to detect or otherwise identify a potential unintended rotation by the rotor of the motor that is not characteristic of boundary error, at which point the monitoring process 700 enters a continuous monitoring mode for a finite duration of time. In the periodic monitoring mode, the monitoring process 700 determines or otherwise identifies whether the motor is being operated (task 702). While the motor is not being operated, the monitoring process 700 activates or otherwise enables the rotor sensing arrangement, samples or otherwise obtains the current outputs of the rotor position sensors, and determines whether a potential unintentional rotation of the motor rotor has occurred based on the obtained sensor outputs (tasks 704, 706, 708).

Referring again to FIGS. 4-5, in exemplary embodiments, the motor control module 402 includes an output flag (e.g., a pin, a terminal or the like) that indicates whether the motor control module 402 is operating the motor driver module 404 and/or motor 407, 500. In this regard, in response to receiving a dosage command, the motor control module 402 sets the output flag to a logic state associated with the motor 407, 500 being operated (e.g., a logical high voltage or logic '1') while controlling the motor driver module 404 to operate the motor 407, 500 in accordance with the dosage command. After operating the motor 407, 500 to achieve the dosage command, the motor control module 402 deactivates or otherwise disables both the rotor sensing arrangement 410 and the motor driver module 404, such that the rotor sensing arrangement 410 and the motor 407, 500 are effectively disconnected and do not consume current from the energy source 403, and sets the output flag to the opposite logic state (e.g., logic '0').

In exemplary embodiments, the monitoring control module 432 is configured to monitor the output flag of the motor control module 402 and determine whether the motor is being operated based on the output flag. When the monitoring control module 432 determines that the motor 407, 500 is not being operated (e.g., the output flag corresponds to logic '0'), the monitoring control module 432 activates or otherwise enables the rotor sensing arrangement 410 and/or Hall sensors 508, 510, 512 (e.g., by providing a logical high voltage to an enable input of the sensors), such that the rotor sensing arrangement 410 and/or Hall sensors 508, 510, 512 are powered on and consume current (or power) from the energy source 403 that enables the rotor sensing arrangement 410 and/or Hall sensors 508, 510, 512 to detect the current position (or orientation) of the rotor magnet 506. The boundary noise filtering module 434 samples the sensor outputs, and if there is no stored reference sensor output state and the sampled sensor output state is not an invalid state, the boundary noise filtering module 434 stores the sensor output state in a first register associated with an initial reference sensor output state and determines that no potential unintentional rotation has occurred.

Referring again to FIG. 7 and with continued reference to FIGS. 1-6, in the periodic monitoring mode, when a potential unintended rotation is not identified, the monitoring process 700 continues by disabling or otherwise deactivating the rotor sensing arrangement and waiting for a delay period before the next periodic polling of the rotor sensing arrangement (tasks 710, 712). In this regard, the monitoring control module 432 deactivates or otherwise disables the rotor sensing arrangement 410 and/or Hall sensors 508, 510, 512 (e.g., by providing a logical low voltage to an enable input of the sensors), such that the rotor sensing arrangement 410 and/or Hall sensors 508, 510, 512 are powered off and effectively disconnected from the energy source 403 and do not consume current (or power) from the energy source 403. The monitoring control module 432 waits for a delay period before repeating the tasks of determining whether the motor 407, 500 is being operated and polling the rotor sensing arrangement 410 (e.g., tasks 702, 704, 706). In accordance with one embodiment, the delay period between successive polling in the periodic monitoring mode is equal to one second.

In exemplary embodiments, the loop defined by tasks 702, 704, 706, 708, 710 and 712 repeats throughout operation of the fluid infusion device until determining either that the motor is being operated or that a potential unintentional rotation has occurred. When the motor is being operated, the illustrated monitoring process 700 resets or otherwise initializes one or more elements of the monitoring module used to track rotation of the motor before the next periodic polling is performed (task 714). In this regard, when the monitoring control module 432 determines that the motor 407, 500 is being operated (e.g., the output flag corresponds to logic '1'), the monitoring control module 432 resets reference sensor output states maintained by the boundary noise filtering module 434, for example, by writing zero or some other null value to the registers of the boundary noise filtering module 434. Additionally, the monitoring control module 432 resets one or more counters of the counter arrangement 436, such as, for example, the rotation counter and the net rotational displacement counter. When the motor is being operated, the monitoring control module 432 also waits for the delay period (e.g., one second) before repeating the tasks of determining whether the motor 407, 500 is being operated and polling the rotor sensing arrangement 410 (e.g., tasks 702, 704, 706). It should be noted that in exemplary embodiments, when the motor control module 402 operates the motor 407, 500 to achieve a commanded dosage, the motor control module 402 activates or otherwise enables the rotor sensing arrangement 410 to confirm that the measured rotation of the rotor 504 of the motor 407, 500 corresponds to the expected (or commanded) rotation and may thereby detect a potential unintentional rotation of rotor 504 based on a deviation between the measured rotation and the expected rotation. For example, the motor control module 402 may detect a potential unintentional rotation of rotor 504 when the measured rotation is in a direction opposite the expected rotation, when a difference between the measured rotation and the expected rotation exceeds a threshold value, when the rotor sensing arrangement 410 outputs an invalid state, or the like.

As described above, during the periodic monitoring mode, the boundary noise filtering module 434 samples the current sensor outputs and compares the most recently obtained sensor output state to the stored reference states to detect or otherwise identify unintentional rotation of the rotor 504 that is unlikely to be attributable to magnetic field boundary alignment error. In this regard, if the most recently obtained sensor output state is equal to the stored initial reference sensor output state, the boundary noise filtering module 434 determines that no potential unintentional rotation has occurred and provides an output signal (e.g., a logical low voltage or logic '0') that causes periodic monitoring mode to be maintained by the monitoring control module 432. If the most recently obtained sensor output state is equal to one detectable incremental rotation of the rotor 504 relative to the stored initial reference sensor output state and the stored initial reference sensor output state is the only stored reference sensor output state maintained by the boundary noise filtering module 434, the boundary noise filtering module 434 stores that most recently obtained sensor output state in a register associated with a boundary error reference sensor output state and continues provides an output signal that causes periodic monitoring mode to be maintained by the monitoring control module 432. Thereafter, when the most recently obtained sensor output state is equal to either the stored initial reference sensor output state or the stored boundary error reference sensor output state, the boundary noise filtering module 434 determines that any rotation of the rotor 504 is likely attributable to magnetic field boundary alignment error and continues providing an output signal that causes periodic monitoring mode to be maintained by the monitoring control module 432.

When the most recently obtained sensor output state is not equal to either the initial reference sensor output state obtained during the initial periodic polling or the boundary error reference sensor output state, the monitoring process 700 determines that a potential unintentional rotation has occurred enters a continuous monitoring mode for a finite duration of time during which the rotor sensors are continuously enabled and sampled to confirm whether an actionable (or non-negligible) unintentional rotation of the rotor has occurred (tasks 716, 718, 720). In this regard, when the sampled sensor output state obtained by the boundary noise filtering module 434 is not equal to either reference sensor output state stored by the boundary noise filtering module 434, the boundary noise filtering module 434 determines that a potential unintentional rotation has occurred and provides an output signal (e.g., a logical high voltage or logic '1') that causes continuous monitoring mode to be entered by the monitoring control module 432. In the continuous monitoring mode, the monitoring control module 432 maintains the rotor sensing arrangement 410 activated or otherwise enabled for a finite duration of time and enables the counter arrangement 436 to sample and track changes in the sensor output states. For example, in one embodiment, the enabled rotor sensing arrangement 410 generates an interrupt whenever one or more of the Hall sensors 508, 510, 512 exhibits a change in output state, wherein the monitoring module 430 and/or counter arrangement 436 automatically samples the outputs of the rotor sensing arrangement 410 and/or Hall sensors 508, 510, 512 in response to the interrupt. In alternative embodiments, the outputs of the rotor sensing arrangement 410 and/or Hall sensors 508, 510, 512 may be continuously sampled at a sampling rate supported by the monitoring module 430 and/or counter arrangement 436, with the detection logic 438 continuously comparing the values of the counters in the counter arrangement 436 to their respective threshold values to identify whether any of the thresholds have been exceeded. In exemplary embodiments, the monitoring module 430 and/or detection logic 438 performs the detection process 800 of FIG. 8 during the continuous monitoring mode to detect or otherwise identify an actionable unintentional rotation.

In accordance with one or more embodiments, the monitoring control module 432 implements a timer or another similar feature to regulate the duration of the continuous monitoring mode, such that in the absence of an actionable unintentional rotation being detected by the detection logic 438, the monitoring control module 432 maintains the rotor sensing arrangement 410 and/or Hall sensors 508, 510, 512 and the counter arrangement 436 enabled to continuously obtain the sensor output state for that entire duration of time. In this regard, when the monitoring control module 432 determines that the finite duration for the continuous monitoring mode has elapsed or otherwise expired without detecting an actionable unintentional rotation, the monitoring control module 432 disables or otherwise deactivates the rotor sensing arrangement 410 and/or Hall sensors 508, 510, 512 and reverts back to the periodic monitoring mode (e.g., tasks 710, 712). As described above, in accordance with one or more embodiments, when the finite duration for the continuous monitoring mode elapses without detecting an actionable unintentional rotation, the monitoring control module 432 may obtain a compensation value from the net rotational displacement counter and provide the compensation value to the motor control module 402 for adjusting subsequent delivery commands to compensate or otherwise account for such minor unintentional rotations.

Still referring to FIG. 7, in exemplary embodiments, when the monitoring process 700 detects an actionable unintended rotation, the monitoring process 700 initiates one or more remedial actions (task 722). For example, as described above, the monitoring control module 432 may generate or otherwise provide a logical high notification signal to the pump control system 420 to notify the pump control system 420 of the unintentional rotation. Additionally, in some embodiments, the monitoring control module 432 may also notify the pump control system 420 of the type of unintentional rotation (e.g., which of the counters of the counter arrangement 436 triggered the notification). In response receiving indication of an actionable unintentional rotation from the monitoring control module 432, the pump control system 420 may initiate or otherwise perform one or more remedial actions, such as, for example, generating an auditory and/or visual alert to the user of the infusion device 400 (e.g., via display element 126), commanding the motor control module 402 to rewind the motor 107, 407, 500 (and thereby the slide 106, 406 and plunger 117, 417) and prevent subsequent delivery, modifying subsequent dosage commands, and the like. It should be appreciated that the subject matter described herein is not limited to any particular remedial action, or any particular combinations or sequences thereof.

Figure 8:
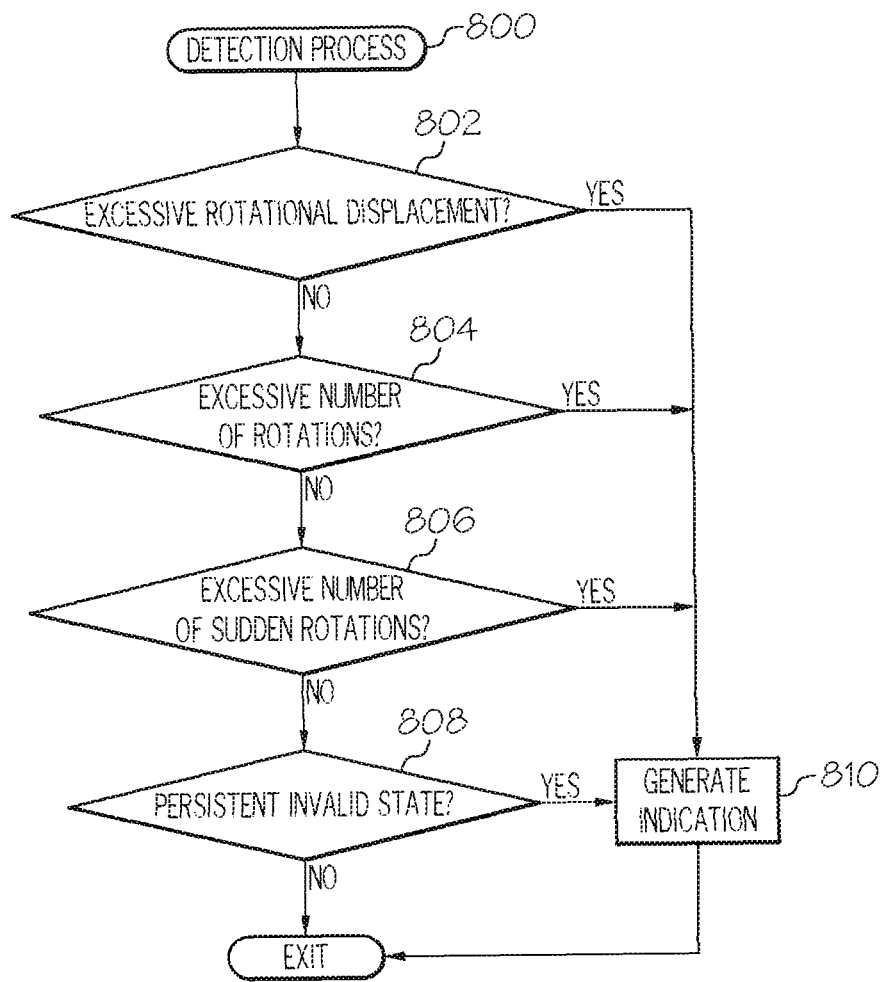
FIG. 8 is a flow diagram of an exemplary detection process suitable for use with the monitoring process of FIG. 7.

FIG. 8 depicts an exemplary detection process 800 suitable for implementation by a control system in a fluid infusion device in conjunction with the monitoring process 700 to detect actionable unintentional motor motion during a continuous monitoring mode. The various tasks performed in connection with the detection process 800 may be performed by hardware, firmware, software, or any combination thereof. For illustrative purposes, the following description refers to elements mentioned above in connection with FIGS. 1-6. In practice, portions of the detection process 800 may be performed by different elements of the control system 401, such as, for example, the monitoring module 430, the monitoring control module 432, the counter arrangement 436, and/or the detection logic 438. It should be appreciated that the detection process 800 may include any number of additional or alternative tasks, the tasks need not be performed in the illustrated order and/or the tasks may be performed concurrently, and/or the detection process 800 may be incorporated into a more comprehensive procedure or process having additional functionality not described in detail herein. Moreover, one or more of the tasks shown and described in the context of FIG. 8 could be omitted from a practical embodiment of the detection process 800 as long as the intended overall functionality remains intact.

In the illustrated embodiment, the detection process 800 determines whether an excessive rotational displacement has been observed and generates or otherwise provides an indication of an actionable unintended rotation in response to identifying a rotational displacement that exceeds a threshold (tasks 802, 810). As described above, in exemplary embodiments, the counter arrangement 436 includes a net displacement counter that tracks the net rotational displacement of the rotor 504 by accumulating the rotational difference between successive sampled sensor output states. For example, if the initially sampled sensor output state indicates the rotor 504 is oriented at '100' (with Hall sensor 508 aligned with the rotor magnetic north and Hall sensors 510, 512 aligned with the rotor magnetic south as illustrated in FIG. 5) and the next sampled sensor output state indicates the rotor 504 is oriented at '010' (with Hall sensor 510 aligned with the rotor magnetic north and Hall sensors 508, 512 aligned with the rotor magnetic south), the value of the net displacement counter increases by two to indicate that the rotor 504 was displaced two detectable incremental rotations in the clockwise direction relative to its initial rotational position. In this regard, if the next sampled sensor output state were to indicate the rotor 504 is oriented at '011' (with Hall sensors 510, 512 aligned with the rotor magnetic north and Hall sensor 508 aligned with the rotor magnetic south), the value of the net displacement counter would increase by one (e.g., an accumulated value of three) to indicate that the rotor 504 was displaced one detectable incremental rotation in the clockwise direction relative to its preceding rotational position. Conversely, if the next sampled sensor output state were to indicate the rotor 504 is oriented at '110' (with Hall sensors 508, 510 aligned with the rotor magnetic north and Hall sensor 512 aligned with the rotor magnetic south), the value of the net displacement counter decreases by one (e.g., an accumulated value of one) to indicate that the rotor 504 was displaced one detectable incremental rotation in the counterclockwise direction relative to its preceding rotational position. As described above, the detection logic 438 compares the magnitude of the value of the net displacement counter to a threshold value corresponding to the tolerable unintentional rotational displacement in either rotational direction, and generates a logical high indication signal when the net displacement value exceeds the threshold value. For example, in one embodiment, the detection logic 438 detects excessive rotational displacement when the magnitude of the net rotational displacement counter is greater than four detectable incremental rotations in either the clockwise or the counterclockwise direction.

Still referring to FIG. 8, the detection process 800 also determines whether an excessive number of movements have been observed and generates or otherwise provides an indication of an actionable unintended rotation in response to identifying that the number of movements exceeds a corresponding threshold (tasks 804, 810). As described above, in exemplary embodiments, the counter arrangement 436 includes a rotation counter that counts the number of changes in the sensor output state by comparing the most recently obtained sensor output state to the preceding sensor output state. In this regard, the rotation counter increments by one each time the most recently obtained sensor output state is different from the preceding sensor output state. As described above, the detection logic 438 compares the value of the rotation counter to a threshold value corresponding to the tolerable unintentional movements in any rotational direction, and generates a logical high indication signal when the counted number of changes in the sensor output state exceeds the threshold value. For example, in one embodiment, the detection logic 438 detects an excessive number of motor movements when the value of the rotation counter is greater than ten.

In exemplary embodiments, the detection process 800 also determines whether an excessive number of sudden movements have been observed and generates or otherwise provides an indication of an actionable unintended rotation in response to identifying the number of sudden movements exceeds a corresponding threshold (tasks 806, 810). As described above, in exemplary embodiments, the counter arrangement 436 includes a sudden motion counter that counts the number of times the sensor output state changes by three detectable incremental rotations in either rotational direction relative to the preceding sensor output state. For example, if the initially sampled sensor output state indicates the rotor 504 is oriented at '100' and the next sampled sensor output state indicates the rotor 504 is oriented at '011' (with Hall sensors 510, 512 aligned with the rotor magnetic north and Hall sensor 508 aligned with the rotor magnetic south), the value of the sudden motion counter increments by one to indicate that the rotor 504 was displaced three detectable incremental rotations (or half a revolution) relative to its initial rotational position. As described above, the detection logic 438 compares the value of the sudden motion counter to a threshold value corresponding to the tolerable unintentional sudden movements in any rotational direction, and generates a logical high indication signal when the counted number of sudden movements exceeds the threshold value. For example, in one embodiment, the detection logic 438 detects an excessive number of sudden movements when the value of the sudden motion counter is greater than three.

In the illustrated embodiment, the detection process 800 also determines whether excessive invalid sensor states have been observed and generates or otherwise provides an indication of an actionable unintended rotation in response to identifying persistent invalid sensor states (tasks 808, 810). In this regard, while the invalid sensor state does not necessarily mean that the rotor 504 has rotated, by virtue of the rotor magnet 506, it is likely that a persistent external magnetic field that is capable of interfering with the rotor sensing arrangement 410 and/or Hall sensors 508, 510, 512 detecting the rotor magnetic field for an extended duration of time is also capable of displacing the rotor 504 relative to what its rotational position (or orientation) was prior to the presence of the external magnetic field. As described above, in exemplary embodiments, the counter arrangement 436 includes an invalid state counter that counts the number of times the sensor output state corresponds to an invalid sensor output state (e.g., '000' or '111'), and the detection logic 438 compares the value of the invalid state counter to a threshold value corresponding to the tolerable duration for a persistent external magnetic field, and generates a logical high indication signal when the counted number of invalid sensor output states exceeds the threshold value. In some embodiments, the threshold value may be determined or otherwise chosen based on a sampling rate implemented by the counter arrangement 436 such that the threshold value corresponds to the tolerable duration. For example, in one embodiment, the threshold value is chosen to be equal to the number of samples capable of being obtained over a duration of two seconds, such that the detection logic 438 provides the logical high indication signal when the counted number of invalid states indicates the external magnetic field has persisted for at least two seconds.

Referring to FIGS. 7-8, and with continued reference to FIGS. 1-6, in exemplary embodiments, the monitoring module 430 performs the detection process 800 continuously and/or repeatedly throughout the duration of the continuous monitoring mode to detect an actionable unintentional rotation (e.g., task 718). As described above, when the detection logic 438 indicates that an actionable unintentional rotation is detected (e.g., by generating or otherwise providing a logical high indication signal), the monitoring control module 432 generates or otherwise provides a corresponding notification to the pump control system 420 to enable the pump control system 420 to initiate one or more remedial actions (e.g., task 722).

Referring to FIGS. 1-8, one benefit of the subject matter described herein is that unintentional rotation by the rotor 504 of the motor 107, 407, 500 in a fluid infusion device 100, 400 may be reliably detected in an efficient manner. The rotor sensing arrangement 410 and/or Hall sensors 508, 510, 512 do not continuously consume power (or current) from the energy source 403 during the monitoring process 700 when the motor 107, 407, 500 is not being operated unless a definitive rotation is detected. In this regard, relatively minor rotations that are just as likely to be attributable to magnetic field boundary alignment error as they are likely to be attributable to an external magnetic field are effectively filtered and do not result in the monitoring process 700 entering into a continuous monitoring mode during which the rotor sensing arrangement 410 and/or Hall sensors 508, 510, 512 would otherwise continuously consume power (or current) from the energy source 403. Additionally, the continuous monitoring mode may have a relatively limited finite duration (e.g., five seconds), such that when the continuous monitoring mode is entered, its impact on the power consumption from the energy source 403 may be limited or otherwise restricted, thereby improving the efficiency of the monitoring process 700. Relatively minor unintentional motor rotations may be compensated for by adjusting subsequent delivery commands without generating alerts or otherwise interfering with the user, with various thresholds being utilized to distinguish such minor unintentional rotations from actionable unintentional rotations. Furthermore, when an actionable unintentional rotation is ultimately identified, the type of unintentional rotation or sensor output responsible for generating the notification may be identified and utilized to dynamically determine the appropriate remedial action(s) to be initiated.

The foregoing description may refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. In addition, certain terminology may also be used in the herein for the purpose of reference only, and thus is not intended to be limiting. For example, terms such as "first", "second", and other such numerical terms referring to structures do not imply a sequence or order unless clearly indicated by the context.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An infusion device comprising:
    a motor including a rotor, the rotor having a magnet coupled thereto, wherein rotation of the rotor is configured to provide translational displacement of a plunger in a fluid reservoir;
    a sensing arrangement coupled to the motor, the sensing arrangement comprising one or more sensors to provide output indicative of a detected magnetic field of the magnet when the sensing arrangement is enabled; and
    a module coupled to the sensing arrangement to:
        periodically enable the sensing arrangement to consume current while the motor is idle and disable the sensing arrangement after each enabling; and
        detect potential unintended motion of the motor based on the output from the sensing arrangement while periodically enabling the sensing arrangement.

2. The infusion device of claim 1, wherein the module continuously enables the sensing arrangement for a finite duration in response to detecting the potential unintended motion, determines whether the potential unintended motion exceeds a threshold based on the output from the sensing arrangement while continuously enabling the sensing arrangement, and initiates a remedial action in response to determining the potential unintended motion exceeds the threshold.

3. The infusion device of claim 2, wherein the module determines a number of unintended rotations of the rotor of the motor while the sensing arrangement is continuously enabled and determines the potential unintended motion exceeds the threshold when the number of unintended rotations exceeds a threshold number.

4. The infusion device of claim 2, wherein the module determines a rotational displacement of the rotor of the motor while the sensing arrangement is continuously enabled and determines the potential unintended motion exceeds the threshold when a magnitude of the rotational displacement exceeds a threshold value.

5. The infusion device of claim 2, wherein the module determines a number of sudden rotations of the rotor of the motor while the sensing arrangement is continuously enabled and initiates the remedial action when the number of sudden rotations exceeds a threshold number.

6. The infusion device of claim 1, further comprising an energy source coupled to the sensing arrangement, wherein:
    the sensing arrangement consumes the current from the energy source when the sensing arrangement is enabled; and
    the sensing arrangement is disabled prior to periodically enabling the sensing arrangement.

7. The infusion device of claim 6, further comprising a motor driver module coupled between the energy source and the motor to provide current from the energy source to the motor to operate the motor, wherein the module determines the motor driver module is idle prior to periodically enabling the sensing arrangement.

8. The infusion device of claim 1, wherein the module detects potential unintended rotation of the rotor by:
obtaining an initial sensor output state from the one or more sensors in response to initially enabling the sensing arrangement while the motor is idle; and
determining a difference between a subsequent sensor output state from the one or more sensors and the initial sensor output state is not indicative of alignment of a boundary of the magnetic field of the magnet with a first sensor of the one or more sensors.

9. The infusion device of claim 1, wherein the module detects the potential unintended motion by:
obtaining a reference output state from the sensing arrangement in response to periodically enabling the sensing arrangement; and
identifying the potential unintended motion when a difference between the reference output state and a subsequent output state from the sensing arrangement while periodically enabling the sensing arrangement is not attributable to a boundary error.

10. The infusion device of claim 1, wherein:
the motor includes stator windings;
current does not flow through the stator windings of the motor when the motor is idle; and
the sensing arrangement does not consume current while disabled.

11. A method of detecting potential unintended motion of a motor of an infusion device including the motor configured to provide translational displacement of a plunger in a fluid reservoir, the motor including a rotor, the method comprising:
periodically enabling a sensing arrangement while the motor is idle, the sensing arrangement including one or more sensors providing output indicative of a detected characteristic of the rotor when the sensing arrangement is enabled, wherein periodically enabling the sensing arrangement comprises:
enabling the sensing arrangement to consume current on a periodic basis; and
disabling the sensing arrangement after each enabling; and
detecting potential unintended rotation of the rotor while the motor is idle based on outputs from the one or more sensors when periodically enabling the sensing arrangement.

12. The method of claim 11, further comprising:
obtaining one or more reference sensor output states from the one or more sensors in response to the periodic enabling; and
detecting the potential unintended rotation when a difference between a subsequent sensor output state from the one or more sensors during the periodic enabling is not equal to the one or more reference sensor output states.

13. The method of claim 12, wherein obtaining the one or more reference sensor output states comprises:
identifying an initial sensor output state from the one or more sensors as a first reference sensor output state of the one or more reference sensor output states; and
when a difference between a second sensor output state from the one or more sensors and the first reference sensor output state corresponds to an incremental rotation of the rotor, identifying the second sensor output state as a second reference sensor output state of the one or more reference sensor output states.

14. The method of claim 13, wherein detecting the potential unintended rotation of the rotor comprises detecting the potential unintended rotation when a subsequent sensor output state from the one or more sensors during the periodic enabling is not equal to either the first reference sensor output state or the second sensor output state.

15. The method of claim 13, further comprising obtaining the subsequent sensor output state from the one or more sensors after identifying the second sensor output state as the second reference sensor output state.

16. The method of claim 11, further comprising:
continuously enabling the sensing arrangement for a finite duration while the motor is idle in response to detecting the potential unintended rotation; and
initiating a remedial action based on the outputs from the one or more sensors while continuously enabling the sensing arrangement.

17. The method of claim 16, further comprising:
determining whether the potential unintended rotation is greater than a threshold based on the outputs from the one or more sensors when continuously enabling the sensing arrangement; and
adjusting subsequent operation of the motor to compensate for the potential unintended rotation when the potential unintended rotation is less than the threshold, wherein initiating the remedial action comprises initiating the remedial action in response to determining the potential unintended rotation is greater than the threshold.

18. The method of claim 11, further comprising obtaining an initial reference sensor output state from the one or more sensors upon initiation of the periodic enabling, wherein detecting the potential unintended rotation of the rotor comprises detecting the potential unintended rotation when a difference between a subsequent sensor output state from the one or more sensors during the periodic enabling and the initial reference sensor output state is greater than an incremental rotation of the rotor.

19. The method of claim 11, further comprising resetting one or more counters prior to periodically enabling the sensing arrangement.

* * * * *